United States Patent
Ireland

[11] Patent Number: 6,051,191
[45] Date of Patent: Apr. 18, 2000

[54] MICROPLATES

[75] Inventor: Richard Michael Ireland, Liverton, United Kingdom

[73] Assignees: Porvair PLC, Norfolk, United Kingdom; Wallac Oy, Turku, Finland

[21] Appl. No.: 08/972,024

[22] Filed: Nov. 17, 1997

[30] Foreign Application Priority Data

Nov. 25, 1996 [GB] United Kingdom ............. 9624436

[51] Int. Cl.⁷ .................. G01N 21/03; B01L 3/00
[52] U.S. Cl. ............... 422/102; 356/246; 422/58; 422/73
[58] Field of Search .............. 422/102, 73, 58; 356/246

[56] References Cited

U.S. PATENT DOCUMENTS

| | | |
|---|---|---|
| Re. 34,133 | 11/1992 | Thorne . |
| 2,561,339 | 7/1951 | Chediak . |
| 3,356,462 | 12/1967 | Cooke et al. . |
| 3,999,867 | 12/1976 | Stabell . |
| 4,004,150 | 1/1977 | Natelson . |
| 4,245,052 | 1/1981 | Lund . |
| 4,251,159 | 2/1981 | White . |
| 4,254,223 | 3/1981 | Schuurs et al. . |
| 4,431,307 | 2/1984 | Suovaniemi . |
| 4,498,780 | 2/1985 | Banno et al. . |
| 4,659,222 | 4/1987 | Ekholm . |
| 4,725,388 | 2/1988 | Nelson et al. . |
| 4,948,442 | 8/1990 | Manns . |
| 4,956,150 | 9/1990 | Henry . |
| 5,039,860 | 8/1991 | Yrjönen et al. . |
| 5,048,957 | 9/1991 | Berthold et al. . |
| 5,292,484 | 3/1994 | Kelln et al. . |
| 5,298,753 | 3/1994 | Sonne et al. . |
| 5,319,436 | 6/1994 | Manns et al. . |
| 5,457,527 | 10/1995 | Manns et al. . |
| 5,487,872 | 1/1996 | Hafeman et al. . |
| 5,496,502 | 3/1996 | Thomson . |
| 5,514,343 | 5/1996 | Verwohlt et al. . |
| 5,538,691 | 7/1996 | Tosa et al. . |

FOREIGN PATENT DOCUMENTS

| | | |
|---|---|---|
| 0 106 662 A2 | 4/1984 | European Pat. Off. . |
| 0 147 124 A2 | 7/1985 | European Pat. Off. . |
| 0 181 291 A2 | 5/1986 | European Pat. Off. . |
| 0 415 307 A2 | 3/1991 | European Pat. Off. . |
| 0 449 434 A2 | 10/1991 | European Pat. Off. . |
| 0 571 661 A1 | 12/1993 | European Pat. Off. . |
| 0 597 288 A1 | 5/1994 | European Pat. Off. . |
| 0 606 534 A1 | 7/1994 | European Pat. Off. . |
| 0 648 536 A1 | 4/1995 | European Pat. Off. . |
| 0 649 679 A2 | 4/1995 | European Pat. Off. . |
| 2 110 030 | 5/1972 | France . |
| 2 359 422 | 2/1978 | France . |
| 2 668 831 A1 | 5/1992 | France . |
| 58-11835 | of 1983 | Japan . |
| 1 584 589 | 2/1981 | United Kingdom . |
| WO 83/00047 | 1/1983 | WIPO . |
| WO 93/22657 | 11/1993 | WIPO . |
| WO 94/21379 | 9/1994 | WIPO . |
| WO 94/26413 | 11/1994 | WIPO . |
| WO 95/11082 | 4/1995 | WIPO . |
| WO97/12678 | 4/1997 | WIPO . |

*Primary Examiner*—Arlen Soderquist
*Attorney, Agent, or Firm*—Patterson & Keough, P.A.

[57] ABSTRACT

There is disclosed a microplate affording an array of discrete, separate sample wells in which each sample well consists of a well of a first polymer composition, the well having side walls and a base, and being located in a matrix of a second polymer composition, the second polymer composition being opaque, the said matrix shrouding the side walls of the said well and extending beyond the ends of the side walls of the wells, each well being thermally bonded to the matrix of the second polymer composition, so as to form an integral structure. There is also disclosed a method of making a microplate which comprises moulding an array of discrete separate wells of a first polymer composition on a support and then moulding a matrix of a second polymer composition around the said wells so that the said polymer compositions are thermally bonded to each other and separating the said integral structure from the support whereby the wells have open ends emerging through one face of the structure, and their other ends closed.

29 Claims, 7 Drawing Sheets

MICROPLATES

BACKGROUND OF THE INVENTION

The present invention relates generally to multi-well sample plates, commonly referred to as microtitre plates or microplates, or strips which can be assembled into a carrier frame to produce an analogous component. These microplates are commonly used to hold a large number of samples in a rectangular array of wells, (24 wells (4×6) or 96 wells (8×12) being typical examples), to be assayed using various techniques such as scintillation counting, luminometry, fluorimetry, and kinetics. This invention is particularly, though not exclusively, concerned with applications which utilise microplates in assay techniques which are dependant on the emission of light from the sample, as would occur in scintillation counting, fluorimetry or luminometry, or on the transmission of light through the sample, as would occur in optical densitometry.

When microplates are used to hold samples for analysis using assay techniques which are dependant on the transmission of light through or from said samples, it is important to avoid transmission of light between adjacent samples, so-called "light crosstalk" and loss of light by transmission of light from the peripheral wells of the array, resulting in so-called "edge-effect" signal losses. "Light crosstalk" is extremely undesirable because it means that photons detected in any particular sample well may not have originated from the sample in that particular well. "Edge-effect" is similarly undesirable due to loss of photons from the peripheral sample wells resulting in inconsistent results from these wells. This edge-effect can be compensated for, to a certain extent, by adjustments to the software package of the analytical instruments.

It is the purpose of all assaying techniques to obtain a unique measurement for each sample that is fully representative of that sample. It is therefore necessary, when using multi-well components, to ensure the above mentioned cross-talk and edge-effect are reduced or eliminated altogether.

In certain applications it is necessary to have a transparent wall at the bottom of the sample well. These types of microplates can be used in a variety of instruments utilising photodetectors positioned either directly above the normally open end of the sample well, directly underneath the sample well or with photodetectors in both positions for coincidence measurement. It is obviously necessary in the latter two cases for the bottom of the well to be transparent to allow free passage of photons emitted by the sample.

It is also important in certain assays, which rely on the incubation of biological cell material within the sample wells, that the material from which the wells are manufactured is conducive to cell growth. Again, under certain circumstances, it is desirable for the bottom of the well to be transparent to allow microscopic viewing of adherent cells within the sample well.

Currently available microplates for either type of assay consist typically of a unitary polymer upper plate and a unitary polymer lower plate. The two plates are joined together by ultrasonic welding or similar methods. In this construction, the upper plate defines the side walls of the individual sample wells, and the lower plate defines the bottom walls of these wells. The upper plate is impervious to light, being either pigmented, or transparent but provided with an opaque coating at least on the side walls. The lower plate is transparent for the first type of assay in which transmission of light is monitored by through-viewing, and is generally opaque for the second type in which emission is monitored from above. In this second case the lower plate is made opaque through pigmentation or an opaque coating.

Microplates made as a single moulding with opaque side walls and opaque bottom walls are also known.

EP 571661 in the name of Packard is an example of a microplate which contains "opaque bands" projecting down into the lower plate which are intended to stop light passing from one well to another.

U.S. Pat. No. 5,039,860 in the name of Wallac features sample wells for emission type assays which have transparent bottom walls, for use in conjunction with an upper and a lower photomultiplier assembly. These sample wells are typically made by vacuum thermoforming (deep drawing) from a transparent polymer sheet.

U.S. Pat. No. 5,048,957 utilizes an aluminium matrix having through holes with annular shoulders therein, a transparent cuvette being located in each hole and resting on the said shoulder which defines its position in the through hole. The cuvettes are not bonded to the matrix.

WO 94/26413 provides a vessel or array of vessels in which each vessel has an axis, an open top, side walls and a base, the base incorporating a scintillant substance and the base being adapted for the attachment and/or growth of cells. The side walls are referred to as the main body of the vessel and may be pigmented. The base is attached to the side walls by bonding such as heat welding, injection moulding or ultrasonic welding. If there is any defect in such bonding leakage may occur from the vessel. The pigmenting of the side walls is said to eliminate optical crosstalk. However the transparent base plates are not masked from each other and radiation could leak from one base plate to another.

GB 1584589 discloses a multiwell plate which has a tray or matrix having a multiplicity of compartments in which individual wells are removably located in an upright position. The tray may be made of silicone rubber or foam polymer and the wells of glass or polymer material.

The wells are not bonded to the tray.

It is an objective of the present invention to provide an improved microplate, which includes well inserts with an integral clear base which permits sample viewing and/or measurement of light emissions from the sample, the wells being incorporated into an opaque matrix in such a way that it reduces cross-talk between adjacent wells.

It is an another objective of this invention to provide an improved method for manufacturing the sample wells, individually or as part of the microplate, which is both rapid and efficient.

Other advantages of the invention will become apparent upon reading the detailed description and upon reference to the accompanying drawings.

SUMMARY OF THE INVENTION

In accordance with the present invention, the above mentioned objectives are realised by providing a sample well, which in the described embodiment forms part of a microplate, surrounded along its sides by an opaque matrix as part of an unitary component. In the described embodiment an opaque matrix forms the outer structure of the microplate. This opaque matrix contains a rectangular array of preferably cylindrical holes arranged about the central axes of the microplate. A cylindrical cross section is much preferred for the holes but other cross sections could be used. Light is not able to pass through the walls of the holes. The sample wells themselves are positioned within each of the above mentioned holes and may be manufactured from a material conducive to biological cell growth. The base of each sample well is transparent to allow the transmission of light and is preferably completely shrouded from adjacent wells through protrusions at the top and bottom of the holes which form part of the opaque matrix.

The holes pass orthogonally through the plane of the matrix. These may be afforded in a solid opaque matrix or may be afforded by an array of tubes, the interior of which provide the said holes, the tubes being joined to each other and held in the desired fixed array by interconnecting webs of material.

According to the present invention a sample well or a microplate affording an array of sample wells is provided, in which each sample well consists of a well of a first polymer composition, the well having side walls and a base, and being located in a matrix of a second polymer composition, the said matrix shrouding the side walls of the said well and extending beyond the ends of the side walls of the wells, the second polymer composition being opaque, each well being thermally bonded to the matrix of the second polymer composition, so as to form an integral structure.

In one embodiment the matrix of second polymer composition extends over the whole area of the base of each well.

The first polymer composition may contain a polymer different to that in the second polymer composition. Preferably the first polymer composition is not opaque and most preferably is transparent.

In one preferred embodiment the matrix is made of pigmented polystyrene whilst the wells are made of unpigmented polystyrene which is thus translucent or transparent and may contain a scintillant.

The opacity of the second polymer composition is such as to prevent transmission of the radiation which is being measured (e.g. light or other radiation) from one well to another. The opacity may be achieved by incorporating pigment in the second polymer composition.

The first polymer composition can contain additives, such as scintillators, the efficacy of which is diminished by the presence in the composition of pigments. Similarly the first polymer composition may be made from polymers which encourage adherence and growth of cells, but whose efficacy as a substrate for cell growth is diminished by the presence of pigments.

The invention also extends to a microplate affording an array of sample wells having open tops and transparent bases and side walls in a fixed relationship to each other, in which the sample wells are held in, and thermally bonded to, a matrix of opaque material, the matrix extending at least to the base of each sample well and at least to the opening of each sample well, the wells and matrix forming an integral structure.

Since the structure is integral the assembly process is made much more rapid and there is no risk of the cells falling out of the matrix or being inserted the wrong way up during assembly.

It is preferred that the depth of the sample well is greater than its maximum width. The matrix extends a distance Y beyond the base of the sample well and a distance X beyond the top opening of the sample well. X and Y are each preferably at least 0.1 mm, but preferably not in excess of 0.5 mm, more preferably not in excess of 0.25 mm. Y is preferably greater than or equal to X. Preferably the well is circular so that its maximum width, D, is its diameter. D may be 7.5 mm. The ratio of Y:D and X:D are preferably in the range 1:10 to 1:100 or 1:30 to 1:100, more preferably for a 96 well microplate the ratio of Y:D and X:D is in the range 1:50 to 1:100, e.g. 1:60 to 1:90 or 1:70 to 1:80 e.g. about 1:75.

For 384 well plates D is smaller and Y:X is preferably in the range 1:1 to 2.5:1 and X:D and Y:D are in the range 1:10 to 1:25.

Optionally the depth of the transparent sample well is less than its maximum width and the opaque matrix affords the upper part of the side walls of the sample wells, the depth of the complete sample well being greater than its maximum width.

Optionally the polymer of the sample wells contains a functional additive such as a scintillator. Preferably the polymer of the sample wells has a functional capability relevant to the assay being carried out in the microplate, such as a protein binding capability.

The invention also extends to a method of making the microplate.

Thus according to another aspect of the invention a method of making a microplate comprises moulding an array of discrete separate wells of a first polymer composition on a support and then moulding a matrix of a second polymer composition around the said wells so that the said polymer compositions are thermally bonded to each other and separating the said integral structure from the support whereby the wells have open ends emerging through one face of the structure, and their other ends closed.

In a preferred form of the invention in a method of making a microplate a common core (or a multiplicity of cores which will be called the core cluster) which defines the interior form of each individual well (or multiplicity of wells) is inserted into a primary cavity or mould (or moulds) which defines the external form of each individual well, the temperature of the primary mould or moulds being in the range 10–60° C., a first molten polymer composition is injected into the primary mould or moulds at a pressure of 1000–1500 bar, e.g. over 5 to 10 seconds, the temperature of the first molten polymer composition being in the range 180–260° C., the injected first polymer composition is allowed to cool, e.g. for a further 10 to 20 seconds, so that the first polymer composition solidifies around the common core but is still at above ambient temperature, the primary mould or moulds is opened, the common core or core cluster with the individual wells carried thereon is removed from the primary mould or moulds, the said common core or core cluster and wells is located in a secondary cavity or mould, the surface of the common core or core cluster and the individual wells defining the internal form of the matrix of the second polymer composition, the secondary mould defining the external form of the matrix, the temperature of the secondary mould being in the range 10–60° C., the second molten polymer composition is injected into the secondary mould at a pressure of 1000–1500 bar, e.g. over 5 to 10 seconds, so that it thermally bonds to the wells on the common core or core cluster, the second molten polymer composition being at a temperature of 180–260° C., the injected second polymer composition is allowed to cool, e.g. for a further 10 to 20 seconds, so that the second polymer composition solidifies around the individual wells and forms a thermal bond therewith, the secondary mould is opened, and the microplate is ejected from the common core or core cluster.

Preferably the first polymer composition is transparent polystyrene of a melt flow index in the range 1.5 to 20 and a melting point of 185 to 210° C., and the second polymer composition comprising a polystyrene of a melt flow index in the range 1.5 to 20 and a melting point of 185 to 210° C. and a material which renders the second polymer composition opaque, e.g. 5 to 15% when the opacifying material is white, e.g. $TiO_2$ and 0.2 or 0.5 to 5% when the opacifying material is black, e.g. carbon black, the second polymer composition having a melting point of 185 to 210° C.

In one embodiment the method is such that the second polymer composition does not extend over the closed ends of the wells.

In another embodiment the second polymer composition extends over the whole area of the base of each well. Thus in this embodiment each well is completely enclosed within the matrix with only its top end being available for access.

BRIEF DESCRIPTION OF THE DRAWINGS

The invention may be put into practice in various ways and one specific embodiment will be described to illustrate the invention with reference to the accompanying drawings in which.

DETAILED DESCRIPTION OF PREFERRED EMBODIMENTS

Figure 1:
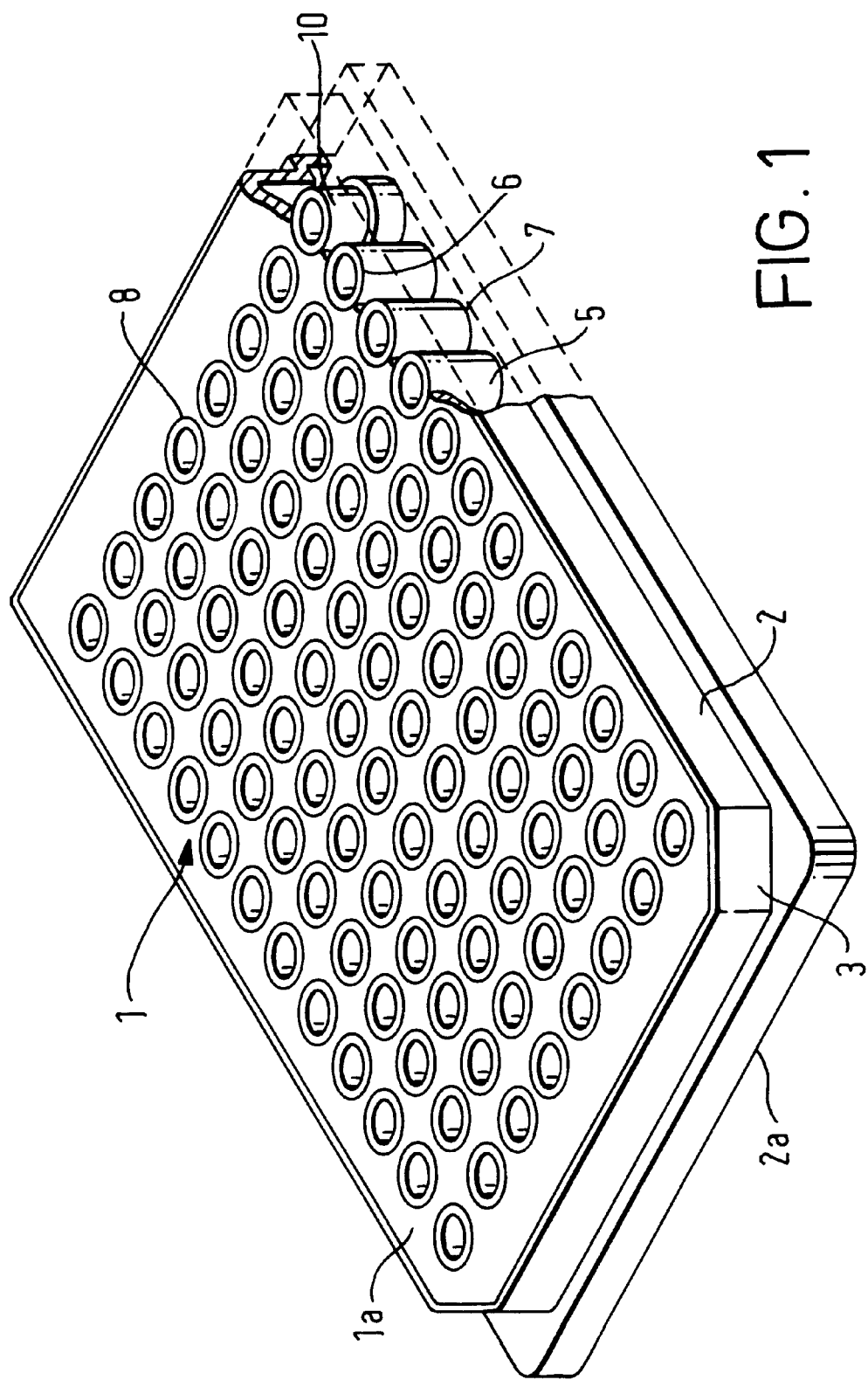
FIG. 1 is an partially sectioned isometric view of a microplate embodying the present invention.

Referring now to the drawings, FIG. 1 shows a microplate embodying the principles of the present invention. The microplate as illustrated comprises an upper web 1 providing an upper surface 1a and side walls 2 (which have a lower edge 2a), which form the basic structure. In the described example the holes are provided by an array of opaque cylindrical tubes 5 having open ends depending from the lower face of the upper surface 1a. These opaque cylindrical tubes 5 are arranged in an 'industry standard' 8×12 rectangular array on 9 millimetre pitch centres about the central axes of and orthogonal to the microplate. The opaque cylindrical tubes 5 are arranged so that the upper end 6 of the tube 5 is positioned to be above the plane of the upper face 1a of the upper web 1 of the described microplate, producing 96 raised beads 8, as illustrated in FIGS. 4 and 5.

The length of the opaque cylindrical tubes 5 is such that the lower end 7 of the said tubes 5 is within the overall height of the illustrated microplate. It is desirable though not essential for there to be a clearance Z between the plane described by the lower ends 7 of the opaque cylindrical tubes 5 and that described by the lower edge 2a of the peripheral walls 2 of the illustrated microplate, as shown in FIG. 4. The components 1, 2 and 5 together provide an opaque matrix 21.

Figure 4:
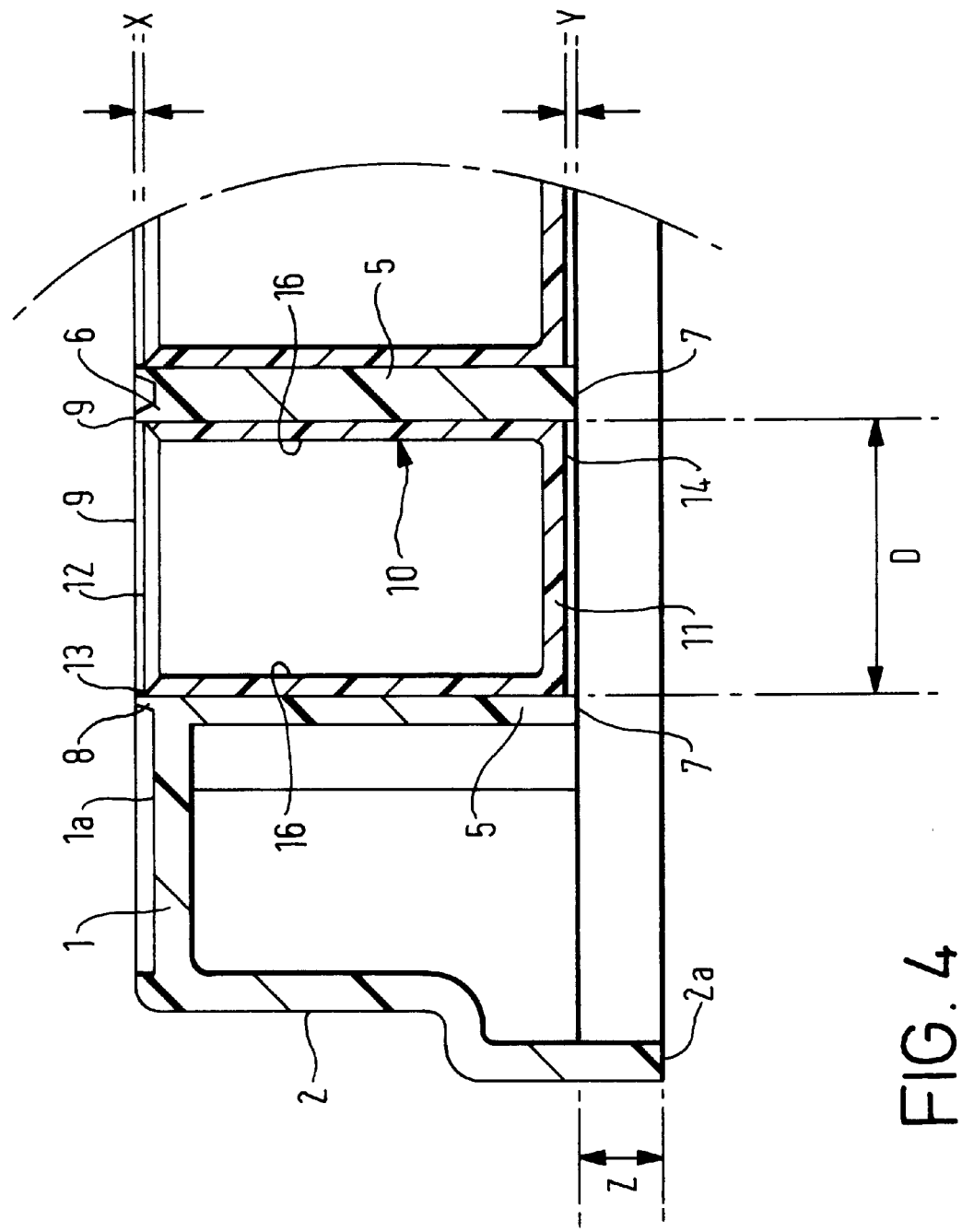
FIG. 4 is a partial cross section on the line III—III of FIG. 2 showing the structure of the microplate of FIG. 1.
Figure 5:
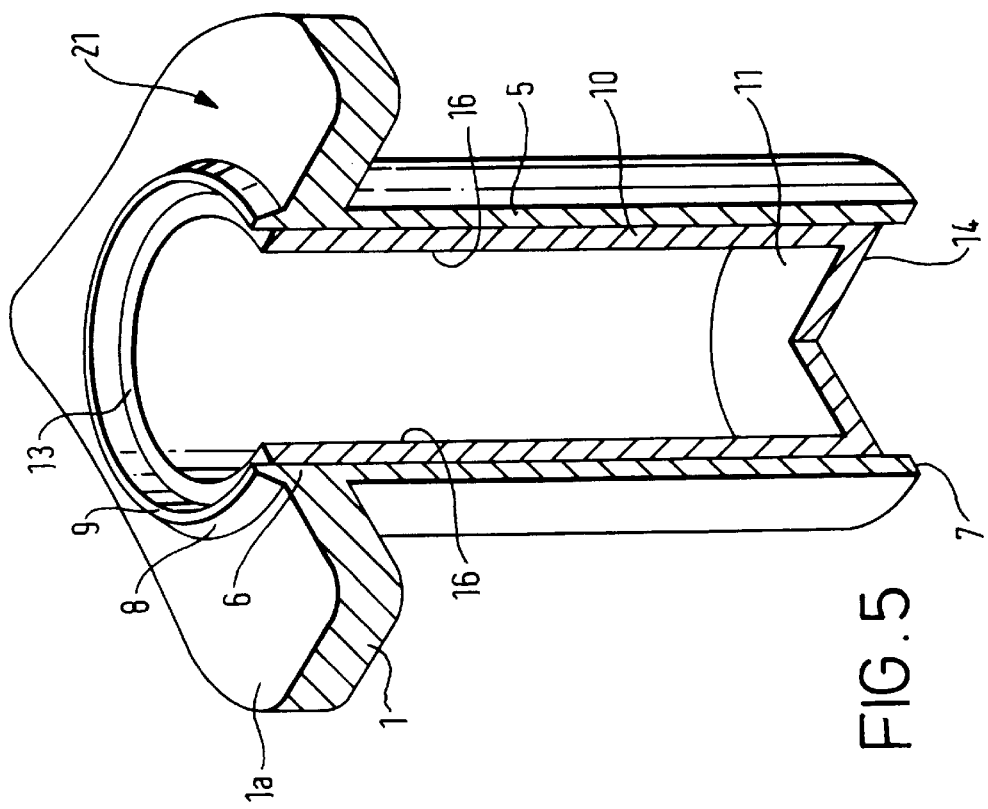
FIG. 5 is a perspective section of a typical sample well embodying the present invention, with a transparent well bottom.

Within each of the above mentioned opaque cylindrical tubes 5 there is positioned a sample well 10 (see FIG. 4). This sample well 10 is secured within the matrix of the illustrated microplate as a result of the unitary manufacturing process utilised.

Figure 2:
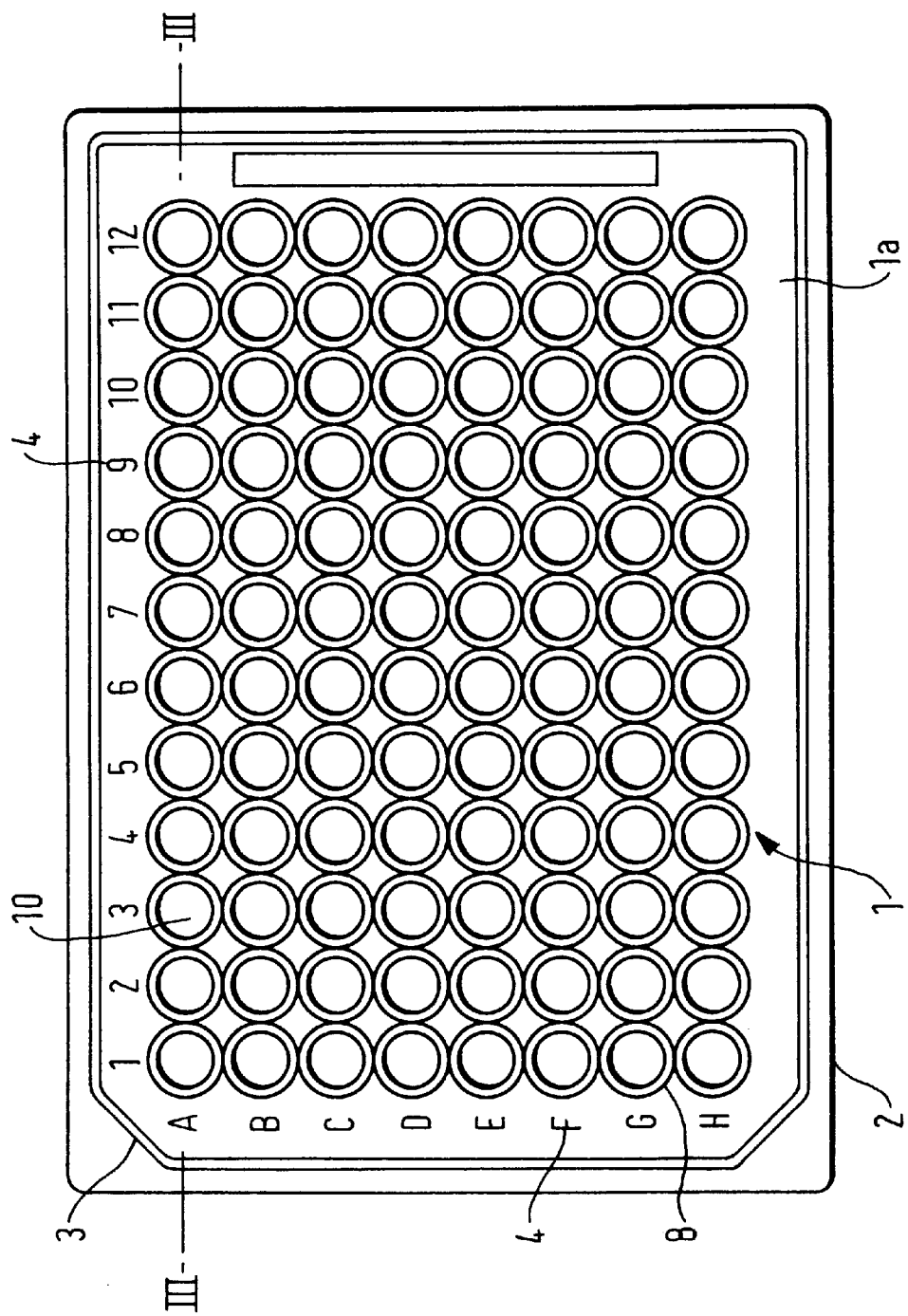
FIG. 2 is a top plan view of the microplate of FIG. 1.

Referring now to FIG. 2, there is illustrated a top plan view of the microplate shown in FIG. 1. Further to the points noted above, this embodiment of the present invention incorporates 'industry standard' features which are of use to the end user. These are the inclusion of chamfered ends 3 to the upper part of the side walls 2 to allow utilisation of commercially available lids and the inclusion of alphanumeric well identification 4. These two features, 3 and 4, do not, in themselves, form any part of the present invention since they are neither novel nor may their inclusion be possible in certain embodiments of the present invention.

Figure 3:
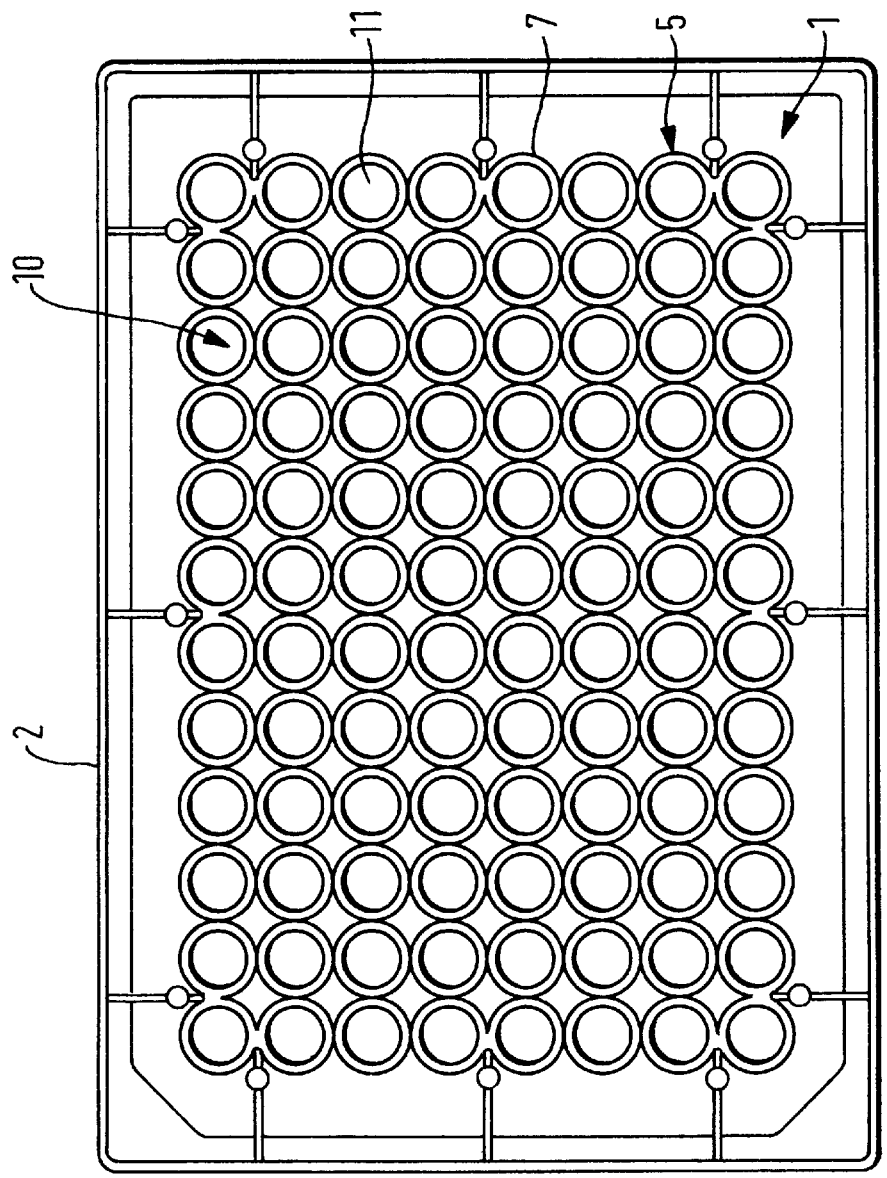
FIG. 3 is a bottom plan view of the microplate of FIG. 1.

Referring now to FIG. 3, there is illustrated a bottom plan view of the microplate shown in FIG. 1. This drawing identifies the relationship between the opaque cylindrical tubes 5 and the sample wells 10, with particular reference to the transparent well bottom or base 11 of each sample well, as well as showing the side walls 16 of the sample wells. This relationship is further illustrated in the partial section of the illustrated microplate, as shown in FIG. 4.

In addition to the points noted above, FIG. 4 identifies the preferred relationship between the sample well 10 and the opaque cylindrical tube 5. It is preferred that the top edge 9 of the raised beads 8 at the top end of an opaque cylindrical tube 5 is in a plane significantly higher than the plane 12 described by the end 13 of the enclosed sample well 10 (leaving a clearance X). The inside face of the well can be chamfered as in FIG. 4 or transverse as in FIG. 5. The advantages of a chamfer are that moulding tools for this shape are easier to make. Similarly the lower end 7 of the opaque cylindrical tube 5 is in a plane significantly lower than the lower surface 14 of the bottom 11 of the sample well 10 (leaving a clearance Y). As previously noted, it is also preferred that there is significant clearance Z between the lower end 7 of the opaque cylindrical tubes 5 and the plane described by the lower edge 2a of the side walls 2 of the microplate, so as to enable the plate to fit into the analytical instrument.

The diameter of the base of the well 10 is D. For a 96 well plate the following Table 1 sets out preferred but non-limiting combinations of values of the dimensions in mms for X, Y and D and the ratios X:D, Y:D and Y:X.

TABLE 1

| Example | X | Y | D | X:D | Y:D | Y:X |
| --- | --- | --- | --- | --- | --- | --- |
| 1 | 0.15 | 0.15 | 7.5 | 1:50 | 1:50 | 1:1 |
| 2 | 0.1 | 0.1 | 7.5 | 1:75 | 1:75 | 1:1 |
| 3 | 0.1 | 0.5 | 7.5 | 1:75 | 1:15 | 5:1 |
| 4 | 0.25 | 0.5 | 7.5 | 1:30 | 1:15 | 2:1 |

Example 1 is a preferred embodiment.

When a plate having more wells, e.g. 384, is produced D is smaller.

For a 384 well plate, the following Table 2 sets out preferred but non-limiting combinations of values of the dimensions in mms for X, Y and D and the ratios X:D, Y:D and Y:X.

TABLE 2

| Example | X | Y | D | X:D | Y:D | Y:X |
|---------|------|------|-----|------|------|------|
| 5 | 0.1 | 0.1 | 2.5 | 1:25 | 1:25 | 1:1 |
| 6 | 0.1 | 0.25 | 2.5 | 1:25 | 1:10 | 2.5:1 |
| 7 | 0.25 | 0.25 | 2.5 | 1:10 | 1:10 | 1:1 |

Figure 6:
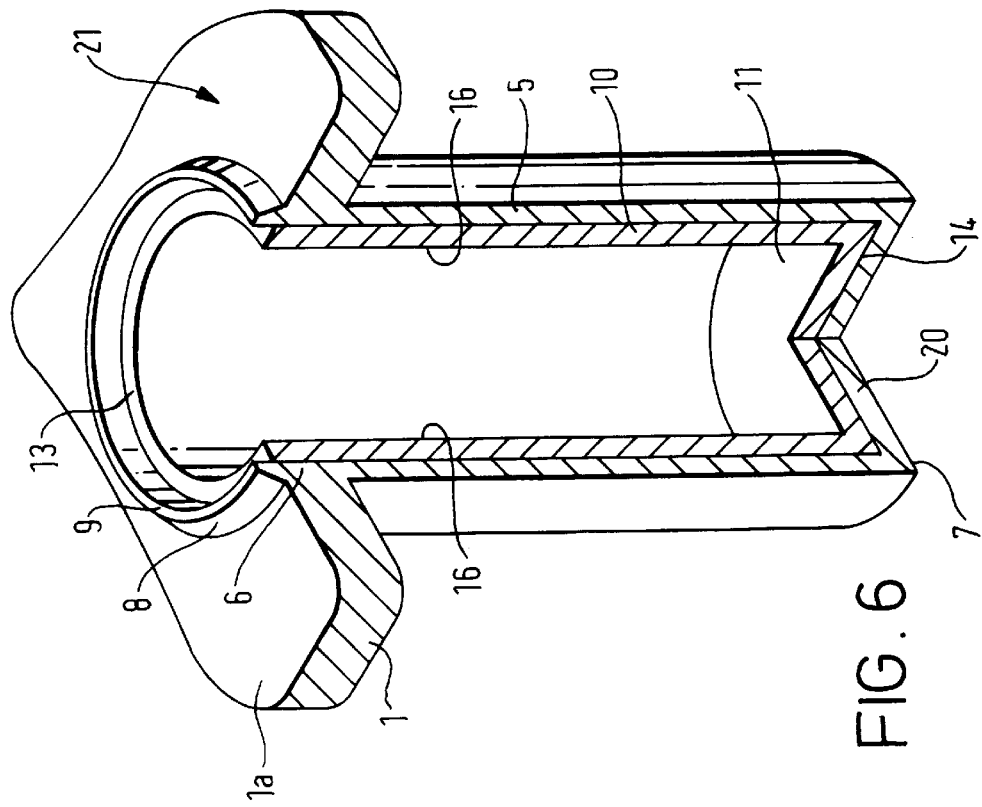
FIG. 6 is a perspective section of a typical sample well embodying the present invention, with an opaque well bottom, (the cross hatching in FIGS. 5 and 6 has been simplified as compared to FIGS. 4, 7 and 8)

With reference to FIG. 5, there is shown a typical single sample well 10 embodying the principles of the present invention. With reference to FIG. 6, there is described a further embodiment of the current invention where the transparent sample well 10 has been encapsulated within the surrounding opaque matrix 21 by extending the lower edges 7 of the opaque cylindrical tube 5 horizontally so that the bottom 11 of the sample well 10 is completely occluded by the region 20.

With regard to the above descriptions the present invention overcomes the problems associated with the so-called "crosstalk" and "edge-effect". In order to restrict light emissions to the well in which they originate, i.e. to prevent the aforementioned crosstalk and edge-effect, the matrix (afforded by 1, 2 and 5) of the microplate illustrated in FIG. 1 is manufactured from an opaque polymeric material which does not allow the transmission of light.

It is normal practice for products manufactured to be used in assays which require the detection of very small amounts of light, for example in liquid scintillation counting, for the pigmentation used to render the polymeric material opaque to be white or light in colour. This selection is made so as to have a high reflectivity off the side walls in order to achieve high counting efficiencies. It is the preferred current practice for these products to be white, due to the ready availability of eminently suitable pigmentation systems. The pigmentation used is generally titanium dioxide, although other white pigments are equally applicable. The pigment is added to the polymer in amounts from 2% to 15% weight. Higher percentage loading gains no significant benefit with regard to increased opacity and actually starts to render the polymer too viscous for injection moulding.

Similarly, in certain types of luminescence and fluorescence assays it is normal practice for the matrix forming the side walls of the wells to be manufactured from an opaque polymer material which has been rendered black by the addition of carbon black, typically added in amounts from 0.2 to 5%, preferably 0.5 to 5% by weight. Pigments in colours other than white and black and fine metal powders can also be used as opacifying materials.

The above method of manufacturing the opaque parts of polymeric microplates is currently accepted commercial practice, be it for opaque microtitre plates or for the well matrix of microplates with transparent bottoms to their wells, of which there are several types commercially available. With reference to these latter type of plates, it is current practice to produce the transparent bottoms as a separate component, large enough to cover the lower side of all ninety-six wells. This component, together with the opaque well matrix is assembled, using proprietary, or commercially available technology to produce the final product.

This method of assembly has several inherent weaknesses:

1. Most current assembly techniques used for volume mass production require that both components be manufactured from generally the same polymeric material.
2. The choice of materials which can be used is limited to those which can be used cost effectively in methods of mass production, whether they are technically correct for the product or conducive to biological cell culture (in the case of products used in assays which require this function).
3. The materials used must be generally resistant to the variety of organic solvents with which they may come into contact.
4. Due to the continuous nature of the transparent component (the part that becomes the bottom of the sample well) it is almost impossible to completely eliminate light cross-talk between adjacent wells, although all manufacturers make great efforts to minimise its effects.
5. Similarly, there are problems of interface design (between the opaque matrix and the transparent base) and the quality and consistency of the assembly, in trying to ensure a reliable bond which eliminates either sample losses within the interface or leakage (liquid cross-talk) between samples in adjacent wells.

The present invention helps to overcome these shortcomings. By way of example, one embodiment of the invention, the microplate as illustrated in FIG. 1, could be manufactured utilising the best or most economic materials available, dependant upon end-user criteria, for both the sample wells 10 and the opaque matrix 21 (comprising the microplate upper surface 1, the side walls 2 and the cylindrical tubes 5). These materials may or may not be polymerically identical or similar, again dependant upon end-user criteria and also the method of manufacture. In the described embodiment the sample wells 10 are arranged in a rectangular array within the opaque matrix 21 whereby they are completely isolated from adjacent wells.

A preferred method of construction, although by no means the only method of achieving such a structure, is to utilise sequential injection moulding techniques whereby the sample wells 10 are located within the matrix 21 during the moulding cycle. Other methods of construction include, non-sequential insert moulding—whereby previously moulded sample wells 10 are used as inserts within the mould producing the opaque matrix 21, and the post-moulding insertion of the sample wells 10 into the opaque matrix 21.

However the techniques used must apply one composition to the other when one or both is sufficiently hot to result in thermal bonding and thus the production of an integral structure.

An example of the sequential injection moulding process is 2-shot moulding utilising a multi-barrel machine with an indexing mould. A typical mould cycle would be as follows:

1. A common core, which is the internal form of the primary shot, here the inside of the wells 10, is inserted into the primary cavity of the mould.
2. Molten polymer to form the transparent sample wells is injected into the primary cavity, here defining the outside surfaces of the wells 10.
3. The mould is cooled to a sufficiently low temperature for the polymer to solidify around the common core, but the product is still warm.
4. The mould is opened with the removal of the common core and first layer of polymer carried thereon. Any excess polymer is removed from the primary cavity for recycling and/or disposal.
5. The mould rotates and presents the common core and the primary moulding to a secondary cavity, having the shape of the matrix 21.
6. The secondary cavity is injected with molten polymer to form the opaque matrix around the transparent sample wells.

7. Simultaneously with step 6, a new common core is inserted into the primary cavity as in step 1 above and the process is started again.
8. The polymer in the secondary cavity is allowed to cool to a sufficient temperature for the component to be solid.
9. The secondary cavity is opened and the finished component is ejected.

The injection of the molten polymer in the second stage onto a still warm product of the first stage ensures excellent adhesion between the walls of the sample cell and the opaque matrix.

EXAMPLE

Figure 7:
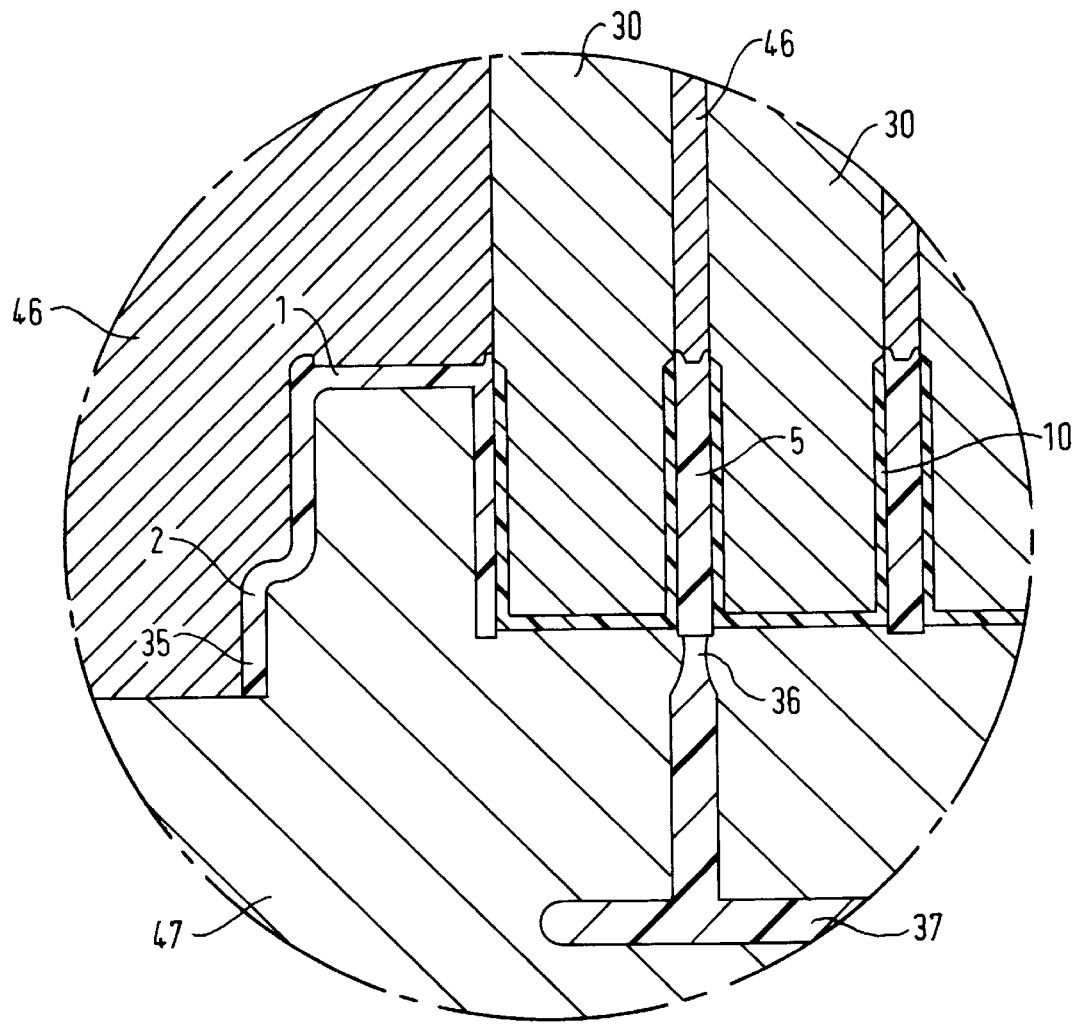
FIG. 7 is a scrap cross-sectional diagramatic view on an enlarged scale of the final moulding making a microplate as shown in FIG. 1

A specific example of the production of a 96 well microplate will now be given with reference to FIGS. 7 and 8. FIG. 7 shows on an enlarged scale the web 1, side walls 2 and two tubes 5 afforded by the matrix with two wells 10 located therein. Also shown is part of a common core 30, which is afforded by a rectangular array of 96 cores which form a primary core cluster, on which the wells 10 are located. FIG. 7 also shows a secondary mould cavity 35 located between the moulds 46 and 47 with injection gates 36 and a runner system 37. The mould component 47 is formed to be able to open so that the gate 36 can separate from the cavity 35 and the runner 37 can also be separated from the remainder of the mould 47. This enables the waste polymer in the runner 37 and the gates 36 to be readily ejected at the end of each moulding cycle. The mould is shown closed in FIG. 7.

Figure 8:
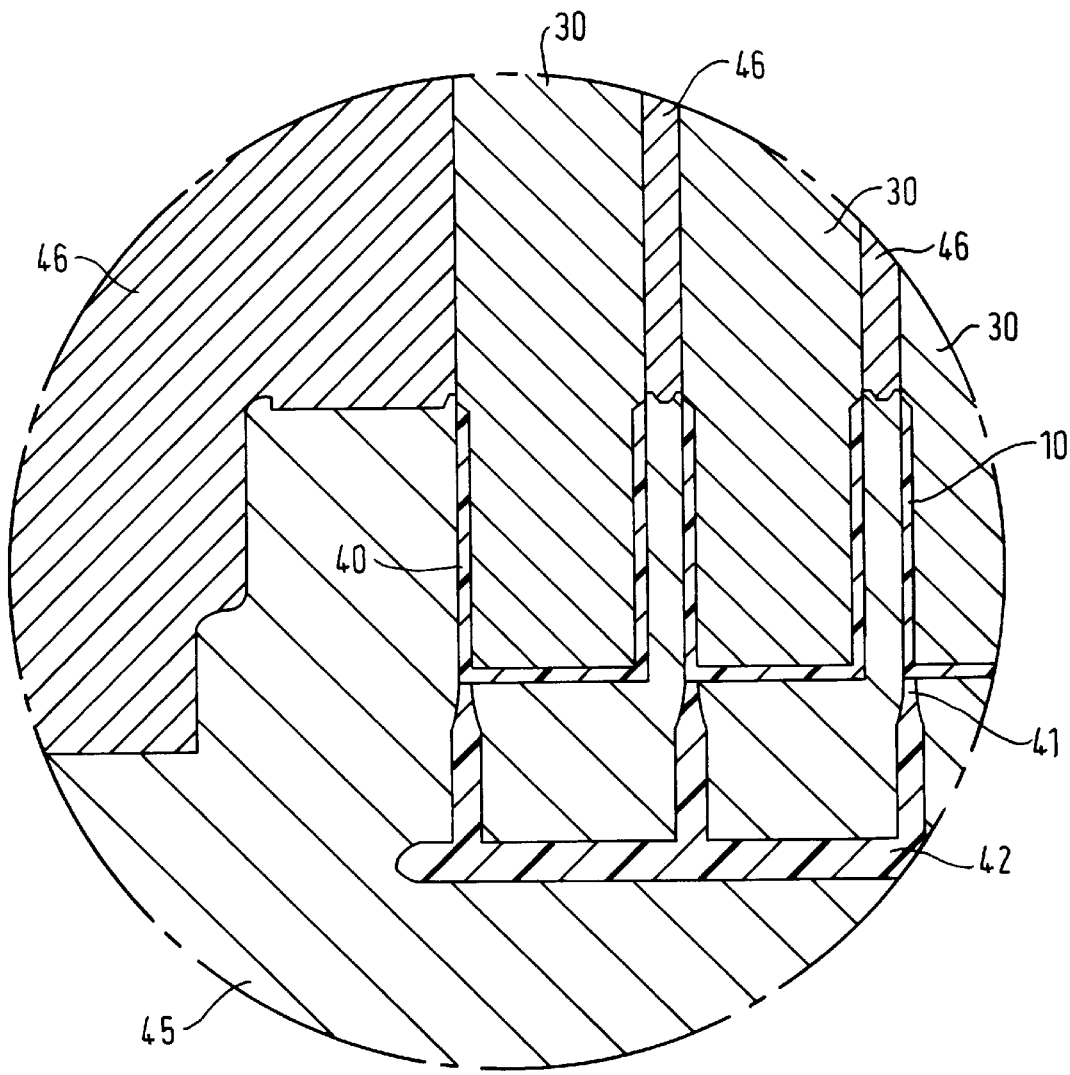
FIG. 8 is a view similar to FIG. 7 showing an earlier stage in the moulding process.

FIG. 8 shows on the same scale as FIG. 7 the common core 30 and the primary cavity 40 formed between the moulds 45 and 46 with its injection gates 41 and a runner system 42. The wells 10 are shown located in the cavity 40 between the core 30 and the mould 45. The mould component 45 is similarly constructed as described for the mould 47 thus also permitting ready ejection of the waste polymer material in the gates 41 and runner 42.

The moulding process is carried out on an Engel 80 tonne microprocessor controlled hydraulic injection moulding machine with multi-colour or multi-material capability afforded by three independently controlled injection cylinders. The mould is mounted within the machine utilising an indexing mould support. The mould temperature is differentially controlled using standard closed-circuit water systems. In practice the fixed parts of the mould (45 and 47) which together with the mould 46 define the primary and secondary cavities (40 and 35) are maintained at a temperature of 40° C. The moving part 46 of the mould is maintained at a temperature of 30° C. and each primary core cluster 30 mounted within the moving part of the mould 46 is cooled to 20° C.

The moulding procedure is as follows. The first polymer composition which is transparent polystyrene with a melt flow index of 12 (measured by the method of ISO/IEC 1133) and a melting point of 190° C. is heated to 220° C. and injected at a pressure of 1200 bar for two seconds into the cavity 40 between the primary core 30 and the mould part 45. The pressure is reduced to 500 bar and maintained for a further 8 seconds. The moulded parts are then allowed to cool for a further 10 seconds. The wells have solidified but are still warm. The mould 45 is opened as described above and the waste polymer material ejected from the gates 41 and runner 42. The primary core cluster 30 is indexed into its next position as shown in FIG. 7 opposite the mould part 47, the parts 46 and 47 between them defining the mould cavity 35. A new set of cores can then be presented to the mould part 45 as shown in FIG. 8 so that the first part of the moulding cycle can be carried out in one mould array whilst the second part of the moulding cycle is carried out in another mould array the process thus continuing in sequence.

Referring now to FIG. 7 the mould parts 46 and 47 are brought together so that a closed cavity 35 is defined between them and the primary core cluster 30 with the wells 10 moulded onto them by the process described above with reference to FIG. 8 are now inserted into the secondary cavity 35. The second polymer composition is made of the same transparent polystyrene described above having a melt flow index of 12 and a melting point of 190° C. this being precompounded with 12% by weight of titanium dioxide which renders the composition opaque. The second polymer composition is heated to a melt temperature of 240° C. and is injected at a pressure of 1250 bar for 2 seconds into the cavity 35 between the mould parts 46 and 47. The pressure is reduced to 800 bar and maintained for a further 8 seconds. The moulded parts are then allowed to cool for a further 10 seconds. The mould part 47 is then opened and the waste polymer material in the gate 36 and runner 37 is ejected and the finished microplate is ejected from the moulds.

The cycle is repeated with simultaneous operation of the primary and secondary stages allowing fully automatic sequential moulding. For this example the dimension D is 7.5 mm and the dimensions X and Y are 0.15 mm. The product which will be referred to as product E1 gives low light cross talk values between adjacent cells and improved counting efficiency.

E1 has been compared with two commercially available products C1 and C2 as to cross talk and counting efficiency values; the results are set out below in Table 1.

C1 is a product made in accordance with U.S. Pat. No. 5,039,860. This is sold in Europe by Wallac Oy as "WALLAC 1450-401 microplate". It consists of a flexible PET plate consisting of wells depending from an integral flat web. Black lines are printed on the web to reduce "light piping" or transmission from well to well through the web. Transmission from the side walls of one well to adjacent wells is blocked by nesting the wells in an apertured opaque plate which provides an opaque tube around each well. The PET plate is flexible and cannot readily be used in automated analysis machines.

C2 is a product sold in Europe by Wallac Oy as "WALLAC 1450-511 or 513 microplate"—the two plates being identical except that 513 is sold in a pre-sterilised form.

C2 is made from an upper white opaque 96 well plate 50 (not shown) which affords the side walls 51 (not shown) of the wells 49 (not shown) of the plate and has the same composition as the matrix described for E1 above i.e. polystyrene containing 12% by weight titanium dioxide. Grooves 53 (not shown) are formed in the lower face 52 (not shown) between each well. The base of the wells is formed of a transparent polystyrene plate 55 (not shown) of the same composition as the wells 10 of E1. This plate has triangular ribs 57 (not shown) extending upwardly and positioned and dimensioned so as to fit into the grooves 53 with their peaks 59 (not shown) contacting the inside face 58 (not shown) of each groove 53. The upper and lower plates are secured to each other by positioning the ribs 57 in the grooves 53 and applying ultrasonic welding energy whereby the peaks 59 act as energy directors and fuse to the faces 58.

The lower face 60 (not shown) of the lower plate is covered by a light absorbing carbon black layer applied by hot foil printing a film pigmented with carbon black. The film covers the whole of the lower face 60 but does not cover the ends of the wells 49.

Cross talk is measured for the central well of a 3×3 square array of wells for the side wells which are closest to the central well (so called "straight cross talk measurement"), and for the two corner wells which are further from the central well (so called "diagonal cross-talk measurement").

Counting efficiency (CE) is also measured. It is the ratio of the actual disintegrations of a known sample per minute (dpm) (i.e. the true activity of a known sample) to the measured activity of the sample in the device under test (i.e. measured counts per minute, cpm) expressed as a percentage.

$$\text{Thus } CE = \frac{\text{dpm}}{\text{cpm}} \times 100$$

The sample tested was a 10 μl (microlitre) tritium labelled biological sample mixed with 190 μl of a proprietary scintillation cocktail (Supermix, sold by Wallac Oy) both unquenched and quenched.

The unquenched counting efficiency is referred to as (UQ). The quenched counting efficiency is referred to as (Q). Values of (Q) given in Table 1 were obtained using tartrazine as the quenching agent or coloured attenuator to produce heavy quenching. In liquid scintillation counting colour quenching is sometimes an unavoidable and unwanted phenomenon because this results in an overall loss of signal. It is therefore important that a sample plate exhibits as high a counting efficiency as possible not only with high efficiency unquenched samples but also with lower efficiency quenched samples.

The results are given in Table 1 below, the counting efficiency measurements being carried out 15 minutes after the samples were mixed.

TABLE 1

| Product | E1 | C1 | C2 |
| --- | --- | --- | --- |
| straight cross talk % | 0.03 | 0.04 | 0.03 |
| diagonal cross talk % | 0.02 | 0.01 | 0.02 |
| counting efficiency (UQ) % | 40.0 | 41.3 | 27.6 |
| counting efficiency (Q) % | 22.4 | 20.3 | 14.5 |

The plates E1 and C2 being rigid can readily be handled by automated analysis machines. The differences in counting efficiencies (UQ) and (Q) are very substantial. The Q values are particularly important. The value 22.4% is a significant and advantageous improvement over the value 20.3 and a remarkable improvement over the value 14.5%.

E1 was also compared with C2 for stability of the cpm values over extended periods of time using the same sample mix as above but a different scintillation cocktail namely Optiphase HiSafe 2 (sold by Wallac Oy) the values of cpm tend to diminish the longer the test is conducted. Lower values reduce the accuracy of the test and accordingly a multiwell plate where the cpm values diminish less with time is advantageous.

Table 2 below gives the elapsed time after mixing and the cpm values for E1 and C2.

TABLE 2

| Plate | cpm value | |
| --- | --- | --- |
| Elapsed time in mins | E1 | C2 |
| 15 | 105021 | 74610 |
| 48 | 105083 | 74137 |
| 82 | 104960 | 73560 |
| 108 | 104062 | 73629 |
| 141 | 103892 | 73333 |
| 167 | 103964 | 72703 |
| 217 | 103563 | 72952 |
| 260 | 102670 | 71776 |
| 319 | 102669 | 71183 |
| 370 | 101602 | 70325 |
| 429 | 101784 | 69365 |
| 480 | 101163 | 67756 |
| 539 | 100618 | 67089 |
| 598 | 99796 | 65933 |
| 649 | 100086 | 64558 |
| 699 | 99599 | 63667 |
| 759 | 99215 | 62284 |
| 843 | 99273 | 60038 |
| 2643 | 93054 | 36784 |

Thus it can be seen from Table 2 that the E1 microplate has a decrease in cpm over 14 hours of only 5.5% whilst C2 has an decrease of 19.5%. In addition after 1.8 days (2643 minutes—44 hours) the cpm of E1 had only decreased by 11.4% whilst the cpm of C2 had decreased by 50.7%. This shows a substantial advantage for the plate in accordance with the present invention.

Cross talk and counting efficiency comparisons were carried out for the E1, C1 and C2 plates using a higher energy test sample, namely iodine 125. The central well contained 10 μl of iodine—125 labelled biological sample and 190 μl of the Supermix scintillation cocktail. The scintillation measurements detect high energy electrons, gamma rays and lower energy electrons and thus the cross talk values are higher. The results are given in Table 3.

TABLE 3

| Product | E1 | C1 | C2 |
| --- | --- | --- | --- |
| straight cross talk % | 0.51 | 0.88 | 0.64 |
| diagonal cross talk % | 0.25 | 0.21 | 0.31 |
| counting efficiency (UQ) % | 63.5 | 62.5 | 59.5 |

It will be observed that E1 gives improved counting efficiency compared to C1 and C2 and overall improved cross talk values.

As stated above, this is not the only method of production of the microplates of the present invention, but is a highly preferred method. An advantage of this method is that different polymer can be used for the transparent sample wells and the surrounding opaque matrix. This is particularly important when the microplates are being used to bind biological substances such as proteins, antibodies and antigens. A polymer particularly suitable for binding, e.g. antibody and/or antigen binding, can be selected for the transparent sample wells and the opaque matrix of the microplate can be made from an alternative, less expensive polymer. This avoids having to make the whole product from the expensive polymer. In addition the side walls of the wells do not have to be pigmented. This may be advantageous when it is wished to have cells grow in and adhere to or antibodies or antigens adhere to the inside walls of the wells. Polystyrene is very effective for such purposes. Pigmentation thereof appears to inhibit antibody and antigen binding to the walls. Thus being able to avoid pigmentation of the walls is an advantage.

A further advantage of the 2-shot method is that scintillators may be added to the system by incorporating them into the molten polymer before injection into the primary cavity. This avoids the need for solvent containing scintillator compositions used either as an addition to the sample under test or as a coating to the inside of the sample well. These solvents may attack the polymer of the microplate, and the coating of the sample well is an additional step and may result in non-uniform results due to variability in the coating process. U.S. Pat. No. 4,568,649 discloses a process by which the fluorescer (scintillator) is introduced to the system via a support structure such as beads. The fluorescer e.g. diphenyloxazole (PPO) is dissolved into a transferring solvent e.g. dimethyl sulfoxide (DMSO) from which the fluorescer is absorbed into the bead and precipitated onto it with water.

With the 2-shot process the scintillators need only be added to the transparent polymer used for the sample wells and not to the polymer for the opaque matrix. This results in a substantial economy in the quantity of scintillators used per plate. It is also thought that the scintillators have more effect when incorporated into a polymer which need not contain any pigmentation as is the case in the present invention.

Typical polymers used in the present invention include polystyrene (PS), polyethylene terephthalate copolymer (PET), polyethylene (PE), styrene acrylonitrile copolymer (SAN), polyvinyltoluene (PVT), polyvinyl chloride (PVC), polycarbonates (PC), acrylics (PMMA), polymethylpentene (PMP), polypropylene (PP) and other polyolefins and copolymers of such materials. Polystyrene is particularly preferred for cell culture applications. Polystyrene surfaces are frequently treated in a plasma chamber (high voltage discharge). This modifies the nature of the surface, increasing its surface energy (surface tension) and polarity, and thereby making it more receptive to cell growth. The plasma treatment for surface activation can also be applied to polymers other than polystyrene, e.g. to PET.

As stated above, the wells and the matrix need not necessarily be constructed of the same polymer. However, when dissimilar polymers are employed, it is necessary to check that they form a satisfactory bond to one another. The adhesion between the two different polymers is not simply a result of the close fit, but also dependent upon the compatibility between their respective surface energies, polarities etc. Particularly preferred combination of polymers are PMP, PP, PE and PET for the well and PP and PS for the matrix, specifically PMP for the well with PP for the matrix, PP, PE or PMP for the well with PS for the matrix and PET for the well with PP for the matrix.

The wells 10 and the tubes 5 form a thermally bonded structure.

The sample wells 10 are completely shrouded from adjacent wells. To achieve this, the height of the sample well 10 is limited, as is illustrated in FIG. 5. The upper edge 13 of the vertical side walls of each sample well 10 is below the plane defined by the top edge 9 of the raised beads 8 of the upper surface 1a of the opaque matrix 21. The lower surface 14 of the transparent bottom 11 to the well 10 is above the plane described by the lower ends 7 of the opaque cylindrical tubes 5.

A further embodiment of the present invention is illustrated in FIG. 6 whereby each transparent sample well 10 has been completely encapsulated within the opaque matrix 21 and its associated opaque cylindrical tube 5, apart from the functionally necessary opening 15 at the top of the said well. This is achieved by providing a horizontal extension 20 at the lower end 7 of the cylindrical tube 5 over the lower face 14 of the transparent bottom 11 to the well 10. This embodiment of the current invention, FIG. 6 will be of particular interest for assays utilising antibody/antigen binding in conjunction with top counting instrumentation. In particular this will be the case where it has been demonstrated previously that the antibodies and antigens are sensitive to the pigmentation systems used in the opaque side walls of the sample cells in existing products. The use of the transparent polymer for the sample wells avoids contact between the sample and the pigmented polymer matrix.

The present invention provides for the use of "biological cell or antibody and/or antigen sample-friendly" wells incorporated into a matrix which can be optimised for the instrumentation or particular assay method. It also allows for the development of assay enhancing or optimising chemistries which can be incorporated into or onto the sample wells themselves—thereby functionally simplifying and enhancing the product for end-users.

Assays in which emission of light is followed by scintillation counting, luminometry or fluorimetry require the presence in the system under test of organic scintillators, organic fluors or other light-emitting systems. As stated above, one advantage of the 2 component structure is the insertion of the scintillators into the polymer for the transparent sample wells alone and not into the polymer for the opaque matrix. This also avoids the scintillators being in contact with pigmented polymer which decrease their level of performance.

Generally, suitable organic fluorescent compounds may be selected, for example, from those described as "organic fluors" and "organic scintillators" in Organic Scintillation Detection, E Schram and R Lombaert, Elsevier Publishing Co., 1963. Useful wavelength shifters (i.e. secondary fluors) are also well known in the scintillation counting art. Preferred among these classes of materials are 2,5-diphenyloxazole (PPO) as the primary fluor and either bis(o-methylstyryl)benzene (bis-MSB) or 9,10-diphenylanthracene or 9,10-dimethylanthracene as the secondary fluor. The primary fluor is preferably present in the range 0.01 to 4 wt %. The secondary fluor is preferably present in the range 0.001 to 0.5 wt %. Energy transfer compounds which enhance the scintillation properties are optional and include compounds like mono- and dialkylnaphthalenes, naphthalene, anthracene, and durene. They can be added in the range 0.01 to 10 wt %. When the fluors are incorporated in the well polymer, energy transfer compounds will not be essential.

The use of additives is not limited to scintillators. Other useful additives could be added to the transparent portion of the microplate. As mentioned above the transparent polymer can be selected to enhance protein-binding. The present invention allows the incorporation of a suitable polymer for the wells without having to use the same polymer for the opaque matrix which could be expensive.

Reference has been made to the wells 10 being transparent. This is much preferred but not essential. The present invention in its broadest aspects permits the wells 10 to have different composition or properties or both from the opaque matrix 21.

In summary the structure of the present invention provides the following advantages. Liquid cross-talk, namely liquid seepage between wells, is avoided by the wells being formed with integral side walls and bases as individual mouldings rather than by the joining of two mouldings. Light cross-talk, namely signal transfer between adjacent wells either via the side walls or the bases, is avoided or reduced by the opaque matrix extending between adjacent wells and beyond their ends. Edge effect, namely loss of light from wells at the edges of the assembly, is avoided or reduced by the matrix shrouding these wells.

I claim:

1. A microplate affording an array of discrete, separate sample wells in which each sample well comprises a well of a first polymer composition, the well having side walls and a base, and being located in a matrix of a second polymer composition, the side walls each having first and second oppositely disposed ends, said matrix shrouding the side walls of each said well and extending beyond both the first and second ends of the side walls of each said well, said matrix leaving at least a portion of the base unshrouded, the second polymer composition being opaque, each well being thermally bonded to the matrix of the second polymer composition, so as to form an integral structure.

2. A microplate as claimed in claim 1, in which the first polymer composition contains a polymer different to that in the second polymer composition.

3. A microplate as claimed in claim 1, or claim 2, in which the first polymer composition is translucent or transparent.

4. A microplate as claimed in claim 1, in which the depth of the sample well is greater than its maximum width.

5. A microplate as claimed in claim 1, in which the matrix extends a distance Y beyond the base of the sample well and a distance X beyond the top opening of the sample well, X and Y each being at least 0.1 mm.

6. A microplate as claimed in claim 1, in which the maximum width of the well is D and the ratio of Y:D and X:D in the range 1:10 to 1:100.

7. A microplate as claimed in claim 6 in which the ratio of Y:D and X:D is in the range 1:50 to 1:100.

8. A microplate as claimed in claim 1, in which each sample well is transparent the depth of the transparent sample well is less than its maximum width and the opaque matrix affords the upper part of the side walls of the sample wells, the depth of the complete sample well being greater than its maximum width.

9. A microplate as claimed in claim 1, in which the polymer of the sample wells contains a functional additive.

10. A microplate as claimed in claim 1, in which the polymer of the sample wells has a functional capability relevant to the assay being carried out in the microplate.

11. A microplate as claimed in claim 1, wherein the first polymer composition is a moulded polymer composition.

12. A microplate as claimed in claim 11, wherein the second polymer composition is a moulded polymer composition.

13. A microplate as claimed in claim 1, wherein said matrix leaves the base entirely unshrouded.

14. A microplate as claimed in claim 1, wherein the base comprises at least a portion of an exterior bottom of the microplate.

15. A microplate as claimed in claim 1, wherein the side walls of the wells each have a thickness of at least 0.10 mm.

16. A microplate as claimed in claim 1, wherein the first polymer composition contains a polymer which is the same as the polymer in the second polymer composition.

17. A microplate as claimed in claim 1, wherein the matrix is made from the second polymer composition which contains a pigment or other opacifying additive.

18. A microplate as claimed in claim 1, wherein the sample wells are made from the first polymer composition which contains an additive relevant to the assay being carried out in the microplate.

19. A microplate as claimed in claim 1, wherein the matrix defines a top surface, further wherein the top surface of the matrix defines raised beads, each raised bead surrounding a respective sample well, a top edge of each raised bead being higher than a remaining portion of the top surface to the matrix.

20. A microplate as claimed in claim 19, wherein one of the first and second oppositely disposed ends of each side wall is a top end, further wherein said remaining portion of the top surface of the matrix is lower than the top end of the side wall.

21. A microplate affording an array of discrete, separate sample wells in which each sample well comprises a well of a first polymer composition, the well having side walls and a base, and being located in a matrix of a second polymer composition, the side walls each having a thickness of at least 0.10 mm and each having first and second oppositely disposed ends, said matrix shrouding the side walls of each said well and extending beyond both the first and second ends of the side walls of each said well, the second polymer composition being opaque, each well being thermally bonded to the matrix of the second polymer composition, so as to form an integral structure.

22. A microplate as claimed in claim 21 in which the matrix of second polymer composition extends over the whole area of the base of each well.

23. A microplate as claimed in claim 21, wherein said matrix contacts only said side walls of said wells.

24. A microplate as claimed in claim 21, wherein each well is thermally bonded to the matrix only along the side walls.

25. A microplate as claimed in claim 21, wherein the base of each sample well is open to the outside of the matrix in two substantially opposite directions.

26. A microplate as claimed in claim 21, wherein each side wall is of substantially uniform thickness from the first end to the second end.

27. A microplate as claimed in claim 21, wherein each side wall defines a substantially vertical internal surface.

28. A microplate as claimed in claim 21, wherein the polymer of the sample wells has a functional capability relevant to the assay being carried out in the microplate.

29. A microplate as claimed in claim 21, wherein the first polymer composition comprises polystyrene.

* * * * *